United States Patent
Kadykowski et al.

(10) Patent No.: US 8,920,456 B2
(45) Date of Patent: Dec. 30, 2014

(54) INSUFFLATION DAMPER FOR ENDOSCOPIC VESSEL DISSECTOR/HARVESTER

(75) Inventors: Randal J. Kadykowski, South Lyon, MI (US); Daniel W. Viitala, Dexter, MI (US)

(73) Assignee: Terumo Cardiovascular Systems Corp., Ann Arbor, MI (US)

(*) Notice: Subject to any disclaimer, the term of this patent is extended or adjusted under 35 U.S.C. 154(b) by 86 days.

(21) Appl. No.: 13/449,380

(22) Filed: Apr. 18, 2012

(65) Prior Publication Data

US 2013/0281780 A1    Oct. 24, 2013

(51) Int. Cl.
| | |
|---|---|
| *A61B 1/12* | (2006.01) |
| *A61M 37/00* | (2006.01) |
| *A61M 3/00* | (2006.01) |
| *A61B 17/34* | (2006.01) |
| *A61B 17/00* | (2006.01) |

(52) U.S. Cl.
USPC ............ 606/190; 600/156; 600/158; 600/159; 604/23; 604/26; 604/43; 604/45; 606/185

(58) Field of Classification Search
CPC ............ A61B 1/00091; A61B 1/00094; A61B 1/00119; A61B 1/00128; A61B 1/015; A61B 1/12; A61B 1/127; A61B 1/128; A61B 2017/320044; A61B 2017/320048; A61B 17/3417; A61B 17/12022; A61M 13/003
USPC ......... 600/104, 106, 114, 121–125, 156–159; 604/23, 26, 43, 45; 606/159, 190, 185, 606/191

See application file for complete search history.

(56) References Cited

U.S. PATENT DOCUMENTS

| | | | |
|---|---|---|---|
| 3,858,572 A | 1/1975 | Binard et al. | |
| 4,048,992 A | 9/1977 | Lindemann | |
| 4,329,985 A * | 5/1982 | Bonchek | ......................... 604/28 |
| 5,006,109 A | 4/1991 | Douglas | |
| 5,139,478 A | 8/1992 | Koninckx et al. | |
| 5,360,396 A | 11/1994 | Chan | |
| 5,514,087 A | 5/1996 | Jones | |
| 7,331,971 B2 | 2/2008 | Kasahara et al. | |
| 7,455,653 B2 | 11/2008 | Ott et al. | |
| 8,048,100 B2 | 11/2011 | Kadykowski et al. | |
| 2009/0306699 A1 * | 12/2009 | Kadykowski et al. | ......... 606/190 |
| 2010/0168520 A1 * | 7/2010 | Poll et al. | ...................... 600/169 |
| 2010/0292533 A1 | 11/2010 | Kasahara et al. | |
| 2011/0196303 A1 | 8/2011 | Chan et al. | |

* cited by examiner

*Primary Examiner* — Ryan Henderson
(74) *Attorney, Agent, or Firm* — Gael Diane Tisack, Esq.; Daryl Newell; McMillan, Sobanski & Todd

(57) ABSTRACT

A vessel harvesting apparatus is provided for removing a vessel from a patient. An endoscopic instrument has a distal end with a vessel harvesting tip and has a proximal end with a handle. The endoscopic instrument has an insufflation channel adapted to receive an insufflation gas from a regulated source at the proximal end. The insufflation channel has an outlet at the distal end adapted to expel the insufflation gas subcutaneously in the patient. A damping device has a flexible bladder with an inside space in fluid communication with the insufflation channel. The inside space has a volume that varies between a rest volume and an inflated volume in response to an amount of insufflation gas flowing to or from the flexible bladder.

2 Claims, 3 Drawing Sheets

INSUFFLATION DAMPER FOR ENDOSCOPIC VESSEL DISSECTOR/HARVESTER

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to devices and methods for endoscopic dissection of a blood vessel within the limb of a patient, and, more specifically, to an insufflation device for maintaining a steady volume around an endoscope for better visualization within a surgical tunnel formed around the blood vessel to be dissected/harvested.

In connection with coronary artery bypass grafting (CABG), a blood vessel or vessel section, such as an artery or vein, is "harvested" (i.e., removed) from its natural location in a patient's body to use it elsewhere in the body. In CABG surgery, the blood vessel is used to form a bypass between an arterial blood source and the coronary artery that is to be bypassed. Among the preferred sources for the vessel to be used as the bypass graft are the saphenous veins in the legs and the radial artery in the arms.

Endoscopic surgical procedures for harvesting a section of a vein (e.g., the saphenous vein) subcutaneously have been developed in order to avoid disadvantages and potential complications of harvesting through a continuous incision. One such minimally-invasive technique employs a small incision for locating the desired vein and for introducing one or more endoscopic harvesting devices. Primary dissection occurs by introduction of a dissecting instrument through the incision to create a working space and separate the vein from the surrounding tissue. Then a cutting instrument is introduced into the working space to sever the blood vessel from the connective tissue and side branches of the blood vessel. The branches may be cauterized using the cutting instrument.

In one typical procedure, the endoscopic entry site is located near the midpoint of the vessel being harvested, with dissection and cutting of branches proceeding in both directions along the vessel from the entry site. In order to remove the desired section of the blood vessel, a second small incision, or stab wound, is made at one end thereof and the blood vessel section is ligated. A third small incision is made at the other end of the blood vessel section which is then ligated, thereby allowing the desired section to be completely removed through the first incision. Alternatively, only the first two incisions may be necessary if the length of the endoscopic device is sufficient to obtain the desired length of the blood vessel while working in only one direction along the vessel from the entry point.

An example of a commercially available product for performing the endoscopic vein harvesting described above is the VirtuoSaph Plus™ Endoscopic Vein Harvesting System from Terumo Cardiovascular Systems Corporation of Ann Arbor, Mich. An endoscopic vein harvesting system of this type is also shown in U.S. Pat. Nos. 7,331,971 and 8,048,100 and U.S. patent application publications 2010/0292533 and 2012/0035606, which are incorporated herein by reference in their entirety.

The dissector tool typically comprises a longitudinal stainless steel or plastic rod with a tip at one end and an operator handle at the other. The tip is tapered to a blunt end and is made of transparent plastic. An endoscope including an optical cable is inserted through the hollow handle and hollow rod to abut the tip to allow for endoscopic viewing during dissection. The dissection proceeds along the perimeter of the vein being harvested to separate it from the surrounding tissue and to expose the side branches of the vein so that they can be severed with the cutting tool.

During dissection and cutting, an insufflation gas such as carbon dioxide is introduced to the subcutaneous space surrounding the blood vessel to improve visualization of the tissue structures within the operative tunnel being created around the vessel. The ability of the tunnel to be inflated is facilitated in part by the use of a trocar at the entry site to provide a partial seal around the endoscopic instrument. Since there is not a 100% trocar seal by design, a continuous supply of the insufflation gas is provided through the endoscopic instrument to be expelled distally at its tip.

The insufflation gas is typically provided by a regulated source known as an insufflation device using a gas cylinder or a pipeline installed in a hospital setting. A target gas flow is set by the clinician, but the flow is normally modulated in order to ensure that a predetermined gas pressure is not exceeded within the surgical tunnel. As a result of turning the gas flow on and off by the insufflation device to avoid over-pressurizing the site while attempting to maintain a sufficient opening of the tunnel, partial pulsations in the insufflation can become evident in the tunnel along with corresponding changes in the visible volume of the tunnel. Consequently, distracting pulsations can sometimes occur in the endoscopic view as seen by the clinician.

SUMMARY OF THE INVENTION

The present invention provides a damper for reducing any fluctuations in the open viewing area of a surgical tunnel during insufflation. In one aspect of the invention, a vessel harvesting apparatus is provided for removing a vessel from a patient. An endoscopic instrument has a distal end with a vessel harvesting tip and has a proximal end with a handle. The endoscopic instrument has an insufflation channel adapted to receive an insufflation gas from a regulated source at the proximal end. The insufflation channel has an outlet at the distal end adapted to expel the insufflation gas subcutaneously in the patient. A damping device has a flexible bladder with an inside space in fluid communication with the insufflation channel. The inside space has a volume that varies between a rest volume and an inflated volume in response to an amount of insufflation gas flowing to or from the flexible bladder.

DETAILED DESCRIPTION OF PREFERRED EMBODIMENTS

Figure 1:
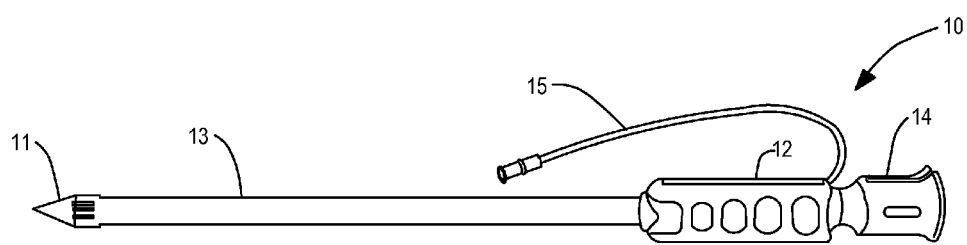
FIG. 1 is a side view of a prior art dissector unit.

Referring to FIG. 1, a dissector unit 10 is shown of a known type for endoscopic dissection of a saphenous vein or other vessel by insertion through an initial incision and then pressing a dissector tip 11 into the fat along the direction of the vessel to separate it from adjacent tissue. Dissector unit 10 has a handle 12 connected to a longitudinal rod 13 having dissector tip 11 at its distal end. A receiver 14 at the end of handle 12 receives an endoscope and optical cable (not shown) for extending through rod 13 to dissector tip 11 which is transparent in order to allow visualization of the vessel and surrounding tissue. An insufflation tube 15 passes through handle 12 and is part of an insufflation gas channel extending to a release hole in or near tip 11. Tube 15 is connected to a source of $CO_2$ or other insufflation gas for filling the cavity adjacent the vessel as it is being formed.

Figure 2:
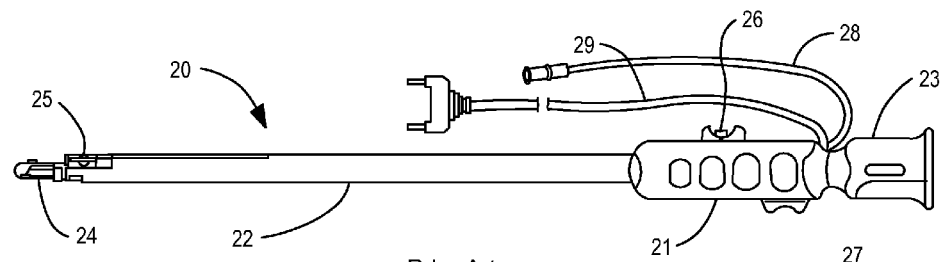
FIG. 2 is a side view of a prior art cutting unit.

After initial blunt dissection around the vessel, a harvester cutting unit 20 as shown in FIG. 2 is used subcutaneously to grasp the vessel being dissected and to sever any branches or connective tissue connecting to the vessel. Harvester 20 has a handle 21 connected to an elongated sleeve member 22 and an endoscope receiver 23. At the distal end of sleeve 22 are a V-keeper 24 for retaining the vessel being dissected and a V-cutter 25 for severing branches. V-keeper 24 is manipulated by V-keeper buttons 26 on handle 21. V-cutter 25 is extended or retracted by manipulating a V-cutter extender button 27 on handle 21. An insufflator tube 28 is adapted to be connected to an insufflation source to deliver the gas to the distal end of sleeve 22 via a gas channel extending between handle 21 at the proximal end and a release hole at the distal end. A bipolar or integrated bipolar cord 29 connects to a source of high frequency voltage, and includes conductors for supplying the voltage to electrodes on V-cutter 25 for cutting and cauterizing the branches and connective tissue.

Figure 3:
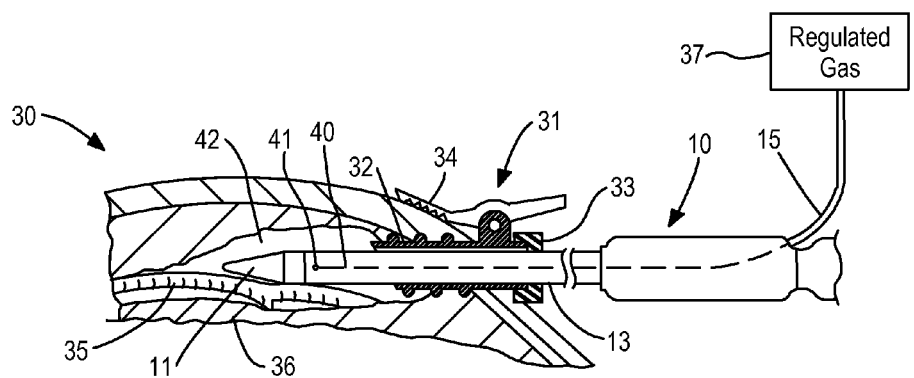
FIG. 3 is a partial cross-sectional view of the dissection of a blood vessel.

FIG. 3 is cross-sectional view showing dissector unit 10 inserted subcutaneously within a lower limb 30 via a trocar 31 from a skin incision in the direction of the inguinal region, for example. Trocar 31 comprises a cylindrical guide tube portion 32 for inserting rod 13, a sealing portion 33, and a fixing portion 34 for fixing the trocar to the skin. Tip 11 and rod 13 of dissector 10 are inserted subcutaneously under the skin via the guide tube portion 32 of trocar 31. An endoscope (not shown) extends all the way to tip 11. Since the inserting direction of dissector 10 is along the direction of a blood vessel 35 being dissected, the operator gradually inserts the dissector so as to dissect peripheral tissue 36 from blood vessel 35 while viewing the endoscope image.

An insufflation gas (e.g., carbon dioxide) may be fed via tube 15 from a regulated insufflation gas source 37. An insufflation unit such as the UHI-3 High Flow Insufflation Unit, available from Olympus Medical Systems Corporation, can be used. An insufflation channel 40 receives the insufflation gas at its proximal end and conveys it to an outlet 41 at its distal end. As blood vessel 35 is dissected from the peripheral tissue, the $CO_2$ gas inflates the area between the dissected tissue and the blood vessel to create an open tunnel 42. Therefore, the field of view of the endoscope is opened wide by gas inflation so that visualization of the internal tissue structures is improved. Following blunt dissection, harvester 20 is inserted through trocar 31 and tunnel 42 is insufflated in the same manner.

Figure 4:
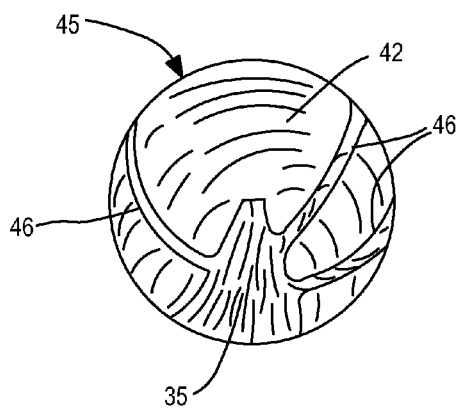
FIG. 4 is an endoscope view into a surgical tunnel around a blood vessel being harvested.

FIG. 4 is an endoscopic view 45 shown on a display that is generated by an endoscopic camera system. In the illustrated embodiment, the endoscopic instrument is part of a vessel harvesting apparatus in which blood vessel 35 is seen within inflated surgical tunnel 42. A plurality of side branches 46 extending from blood vessel 35 can be seen in view 45. Insufflation gas is introduced to maintain good visualization of side branches 46 and other connective tissues during blunt dissection, severing of side branches by a cutter, and any other endoscopic operations being performed.

Figure 5:
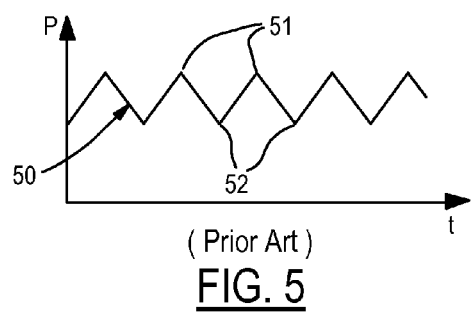
FIG. 5 is a graph showing pressure fluctuations of a conventional insufflation system that can occasionally interfere with visualization within the tunnel.

FIG. 5 shows a pressure curve 50 measured within an insufflation tunnel maintained using a conventional insufflation unit. Pressure varies between maxima 51 and minima 52 as a consequence of using conventional pressure regulation. The pressure variations of FIG. 5 affect view 45 of FIG. 4 by causing changes in the visible structures and/or the size of the region that can be seen, thereby causing occasional distraction or other difficulties during an endoscopic procedure.

Figure 6:
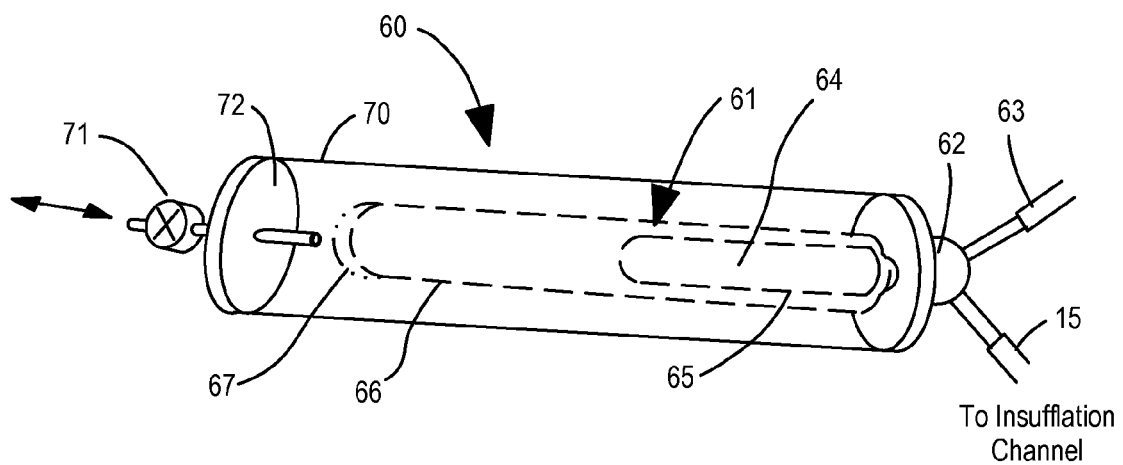
FIG. 6 is a side view of a damper according to one preferred embodiment of the invention.

The present invention employs a damping device 60 as shown in FIG. 6 to reduce or eliminate fluctuations in the endoscopic view. Damping device 60 includes a flexible bladder 61 fluidically coupled via a three-way connector 62 (e.g., a "T"-connector) to an insufflation device via a tube 63 and to the insufflation channel of the endoscopic instrument via tube 15. Flexible bladder 61 has an inside space 64 in fluid communication with the insufflation channel allowing insufflation gas to flow between them. Flexible bladder 61 is preferably comprised of a latex balloon, and inside space 64 has a variable volume that varies between a rest volume shown at 65 and various inflated volumes shown at 66 and 67 in response to an amount of insufflation gas flowing to or from bladder 61 via connector 62. The action of flexible bladder 61 provides a gas buffer to filter out or smooth the pressure variations occurring in the surgical tunnel in response to pulsations of insufflation gas being delivered by the insufflation device.

In a preferred embodiment, flexible bladder 61 may be contained in a substantially rigid shell 70. Shell 70 may be comprised of a clear plastic cylinder with sealed caps at each end, for example. Shell 70 is preferably a sealed enclosure except for 1) a passage where connector 62 enters to join with bladder 61 and 2) a vent valve 71 that couples an interior space 72 within shell 70 to external atmosphere. Vent valve 71 provides a predetermined resistance to a flow of atmospheric air into or out of interior space 72. If desired, vent valve 71 may provide a manually-controlled orifice in order to provide a variable flow resistance to allow calibration of the buffering affect of bladder 61. The manually-controlled orifice within vent valve 71 controls the rate at which flexible bladder 61 can inflate or deflate.

Interior space 72 defines a volume greater than a maximum inflated volume 67 of bladder 61 so that buffering of gas by flexible bladder 61 is not affected by contact with the walls of shell 70.

Based on the damping device shown in FIG. 6, the present invention includes a method of visualizing subcutaneous tissue while harvesting a vessel from a patient as follows. A tip of an endoscopic instrument is inserted subcutaneously into a patient. A regulated supply of insufflation gas is delivered through an insufflation channel in the endoscopic instrument. The inflation gas is expelled out of the tip to inflate a tunnel within the patient. The insufflation channel is coupled to a damping buffer having a variable volume for buffering the insufflation gas, whereby the tunnel maintains a steady visualization region as viewable by the endoscopic instrument. In one preferred embodiment, the damping buffer is comprised of a flexible bladder disposed inside a substantially rigid shell wherein the interior space within the rigid shell is divided between a first space providing the variable volume inside the flexible bladder and a second space between the flexible bladder and the rigid shell. The method may further comprise the step of providing a predetermined resistance to a flow of atmospheric air into or out of the second space, whereby a time constant of the filtering of pressure variations from the insufflation device may be controlled by changing the predetermined resistance to atmospheric air flow. The flow resistance may itself be controlled by manually varying the size of an orifice in the vent valve that couples the second space to atmosphere.

What is claimed is:

1. Vessel harvesting apparatus for removing a vessel from a patient, comprising:
   an endoscopic instrument having a distal end with a vessel harvesting tip comprised of a blunt conical tip for dissecting tissue or a cutter for severing a vessel branch, and having a proximal end with a handle, wherein the endoscopic instrument has an insufflation channel adapted to receive an insufflation gas from a regulated source at the proximal end, wherein the regulated source provides a discontinuous flow of insufflation gas to the proximal end, and wherein the insufflation channel has an outlet at the distal end adapted to expel the insufflation gas subcutaneously in the patient;
   a regulated source of insufflation gas connected to the insufflation channel; and
   a damping device having a flexible bladder, wherein the flexible bladder has an inside space in continuous fluid communication with the insufflation channel, wherein the inside space has a volume that varies between a rest volume and an inflated volume in response to an amount of insufflation gas flowing to or from the flexible bladder, wherein the damping device comprises a vent valve and a substantially rigid shell having an interior space receiving the flexible bladder, wherein the interior space defines a volume greater than the inflated volume, wherein the vent valve has a manually-controlled orifice coupled between 1) an external atmosphere outside the rigid shell and 2) the interior space inside the rigid shell outside of the flexible bladder, wherein the vent valve provides a predetermined resistance to a flow of atmospheric air into or out of the interior space.

2. The apparatus of claim 1 further comprising a T-connector for fluidically coupling the regulated source of insufflation gas, the insufflation channel, and the inside space of the flexible bladder.

* * * * *